United States Patent [19]
Brenner et al.

[11] Patent Number: 6,008,207
[45] Date of Patent: *Dec. 28, 1999

[54] ANHYDROUS ALENDRONATE MONOSODIUM SALT FORMULATIONS

[75] Inventors: Gerald S. Brenner, Norristown; Drazen Ostovic, Lansdale; Earl R. Oberholtzer, Jr., Hatfield, all of Pa.; J. Eric Thies, Scotch Plains, N.J.

[73] Assignee: Merck & Co., Inc., Rahway, N.J.

[*] Notice: This patent is subject to a terminal disclaimer.

[21] Appl. No.: 09/133,200

[22] Filed: Aug. 13, 1998

Related U.S. Application Data

[63] Continuation of application No. 08/973,386, filed as application No. PCT/US96/08284, Jun. 3, 1996, which is a continuation of application No. 08/469,143, Jun. 6, 1995, abandoned.

[51] Int. Cl.$^6$ ................................................ A61K 31/66
[52] U.S. Cl. ............................................................ 514/108
[58] Field of Search .............................. 562/13; 514/108

[56] References Cited

U.S. PATENT DOCUMENTS

| | | | |
|---|---|---|---|
| 4,621,077 | 11/1986 | Rosini et al. | 514/108 |
| 4,922,007 | 5/1990 | Kieczykowski et al. | 562/13 |
| 5,019,651 | 5/1991 | Keiczykowski | 562/13 |
| 5,849,726 | 12/1998 | Brenner et al. | 514/108 |

FOREIGN PATENT DOCUMENTS

| | | |
|---|---|---|
| WO 95/08331 | 3/1995 | WIPO . |
| WO 96/39107 | 12/1996 | WIPO . |

*Primary Examiner*—Raymond Henley, III
*Attorney, Agent, or Firm*—Anthony D. Sabatelli; Melvin Winokur

[57] ABSTRACT

Disclosed is a method for treating and preventing bone loss in patients by administering a formulation of anhydrous alendronate sodium. Also described is a pharmaceutical doage form of said anhydrous alendronate sodium, being anhydrous 4-amino-1-hydroxy-butylidene-1,1-bisphosphonic acid, monosodium salt, in a pharmaceutically acceptable excipient.

4 Claims, No Drawings

ANHYDROUS ALENDRONATE MONOSODIUM SALT FORMULATIONS

CROSS REFERENCE TO RELATED APPLICATIONS

This is a continuation of application Ser. No. 08/973,387, filed Dec. 3, 1997, now U.S. Pat. No. 5,849,726 which in turn is the U.S. National phase application under 35 U.S.C. §371 of PCT application Ser. No. PCT/US96/08284, filed Jun. 3, 1996, which is a continuation of Ser. No. 08/469,143, filed Jun. 6, 1995, now abandoned.

FIELD OF THE INVENTION

The instant invention relates to the use of the anhydrous crystal form of alendronate sodium, i.e., 4-amino-1-hydroxy-butylidene-1,1-bisphosphonic acid monosodium, hereinafter referred to as "anhydrous alendronate sodium" or "AAS", to inhibit bone resorption in human patients.

BACKGROUND OF THE INVENTION

Normal bones are living tissues undergoing constant resorption and redeposition of calcium, with the net effect of maintenance of a constant mineral balance. The dual process is commonly called "bone turnover". In normal growing bones, the mineral deposition is in equilibrium with the mineral resorption, whereas in certain pathological conditions, bone resorption exceeds bone deposition, for instance due to malignancy or primary hyperparathyroidism, or in osteoporosis. In other pathological conditions the calcium deposition may take place in undesirable amounts and areas leading to e.g., heterotopic calcification, osteoarthritis, kidney or bladder stones, atherosclerosis, and Paget's disease which is a combination of an abnormal high bone resorption followed by an abnormal calcium deposition.

U.S. Pat. No. 4,621,077 to Istituto Gentili discloses a method of treating urolithiasis and inhibiting bone reabsorption by the use of 4-amino-1-hydroxybutylidene-1,1-bisphosphonic acid (also named 4-amino-1-hydroxybutane-1,1-bisphosphonic acid) and its salts with an alkali metal, an organic base or a basic amino acid. The compound 4-amino-1-hydroxybutylidene-1,1-bisphosphonic acid is described as being between 100 and 300 times more active than dichloromethane-biphosphonic acid in inhibiting bone reabsorption.

Alendronate sodium, 4-amino-1-hydroxybutylidene-1,1-bisphosphonic acid monosodium trihydrate, is an agent for combating bone resorption in bone diseases including osteoporosis and is described as a composition, method of use and synthesis along with other pharmaceutically acceptable salts in U.S. Pat. Nos. 4,922,007 and 5,019,651 (both assigned to Merck).

However, new crystalline forms of alendronate sodium are constantly being searched for to enable ease of formulation and better pharmacokinetics, e.g., desirable crystal habit, good flow properties, higher solubility, longer duration or quicker onset of action, and improved bioavailability. Particularly what is desired is a new formulation to overcome the gastric irritability associated with the administration of the free acid form of 4-amino-1-hydroxybutylidene-1,1-bisphosphonic acid. This is of particular importance in cases where the patient has a history of gastrointestinal problems prior to recommended alendronate therapy.

SUMMARY OF THE INVENTION

The present invention provides a method for treating and/or preventing bone loss in a subject by the administering to said patient a pharmaceutically effective amount of the anhydrous form of alendronate sodium, 4-amino-1-hydroxybutylidene-1,1-bisphosphonic acid monosodium salt. Because the aqueous pH of the monosodium salt is about 4.4, as compared to the free acid which is about 2.6, there is substantially less gastric irritability associated with the administration of the anhydrous monosodium salt to a human patient.

Also provided is a pharmaceutical composition comprising a pharmaceutically effective amount of anhydrous alendronate sodium, 4-amino-1-hydroxybutylidene-1,1-bisphosphonic acid monosodium salt, in a pharmaceutically acceptable excipient mixture.

DETAILED DESCRIPTION OF THE INVENTION AND PREFERRED EMBODIMENTS

The method disclosed herein can be used to treat humans, particularly females who are post-menopausal, with an osteogenically effective amount of anhydrous alendronate sodium to inhibit bone resorption in need of such treatment. Such need arises locally in cases of bone fracture, non-union, defect, and the like. Such need also arises in cases of systemic bone disease, as in osteoporosis, osteoarthritis, Paget's disease, osteomalacia, multiple myeloma and other forms of cancer, steroid therapy, and age-related loss of bone mass.

The term "inhibition of bone resorption" as used herein, refers to treatment and prevention of bone loss, especially inhibiting the removal of existing bone either from the mineral phase and/or the organic matrix phase, through direct or indirect alteration of osteoclast formation or activity. Thus, the term "inhibitor of bone resorption" as used herein refers to agents that prevent bone loss by the direct or indirect alteration of osteoclast formation or activity and which may increase bone mass in patient treatment populations.

The term "osteogenically effective" as used herein, means that amount which effects the turnover of mature bone. As used herein, an osteogenically effective dose is also "pharmaceutically effective."

The term "treatment" or "treating" as used herein shall mean (1) providing a subject with an amount of anhydrous alendronate sodium sufficient to act prophylactically to prevent the development of a weakened and/or unhealthy state; and/or (2) providing a subject with a sufficient amount of anhydrous alendronate sodium so as to alleviate or eliminate a disease state and/or the symptoms of a disease state, and a weakened and/or unhealthy state.

Pharmaceutical formulations of the invention which include anhydrous alendronate sodium for administration will generally include an osteogenically effective amount of anhydrous alendronate sodium to promote bone growth, in addition to a pharmaceutically acceptable excipient.

The precise therapeutic dosage of anhydrous alendronate sodium will vary with the age, size, sex and condition of the subject, the nature and seventy of the disorder to be treated, and the like; thus, a precise effective amount cannot be specified in advance and will be determined by the caregiver. However, appropriate amounts may be determined by routine experimentation with animal models, as described below. In general terms, an effective dose for alendronate disodium is about 0.01 to 1 mg/kg per day of body weight. Particularly useful dosages are 2.72, 5.44, 10.88 and 43.52 mg per day/per person of anhydrous alendronate monosodium (equivalent to 2.5, 5.0, 10 and 40 mg free acid equivalents) per day per person.

The pharmaceutical composition described herein contains anhydrous alendronate monosodium salt in an amount of about 0.005 to 1.0 gram per gram of composition.

The pharmaceutical compositions according to the present invention containing anhydrous alendronate sodium may be prepared for use in the form of capsules or tablets for oral administration or for systemic use. The compositions are advantageously prepared together with inert carriers such as sugars (saccharose, glucose, lactose), starch and derivatives, cellulose and derivatives, gums, fatty acids and their salts, polyalcohols, talc, aromatic esters, and the like.

The composition can also be prepared by direct compression of a dry mix formulation as described in U.S. Pat. No. 5,358,941 (assigned to Merck & Co. Inc.). Particularly useful diluents in this composition are anhydrous lactose and microcrystalline cellulose.

Some typical pharmaceutical formulations (200 mg oral tablets) containing anhydrous alendronate sodium are shown below:

TABLETS (WHITE), 200 MG

| INGREDIENT | COMPOSITION IN MG/TABLET | | | |
|---|---|---|---|---|
| | 2.5 mg** | 5.0 mg** | 10.0 mg** | 40.0 mg** |
| AAS* | 2.72 | 5.44 | 10.88 | 43.52 |
| Lactose Anhydrous NF | 114.28 | 111.55 | 106.12 | 73.48 |
| Microcrystalline Cellulose NF (Avicel PH 102) | 80.0 | 80.0 | 80.0 | 80.0 |
| Magnesium Stearate NF | 1.00 | 1.00 | 1.00 | 1.00 |
| Croscarmellose Sodium NF (Ac-Di-Sol) | 2.00 | 2.00 | 2.00 | 2.00 |
| Total | 200 | 200 | 200 | 200 |

*AAS, anhydrous alendronate monosodium salt-active ingredient.
**Anhydrous alendronate free acid equivalent, 4-amino-1-hydroxy-butylidene-1,1-bisphosphonic acid.
Note:
The amounts of inactive ingredients may vary ± 10%

The methods and compositions of the invention are useful for treating bone fractures, defects and disorders which result from the pathological conditions of osteoporosis, osteoarthritis, Paget's disease, osteohalisteresis, osteomalacia, bone loss resulting from multiple myeloma other forms of cancer, bone loss resulting from side effects of disuse, other medical treatment (such as steroids), rheumatoid-related and age-related loss of bone mass.

The composition of the instant invention is also useful in lessening the risk of vertebral and non-vertebral fractures in osteoporotic post-menopausal women.

The composition described herein is also useful for the prevention and treatment of periodontal disease (see U.S. Pat. No. 5,270,365); to prevent or treat loosening of orthopedic implant devices; and, to lessen the risk in osteoporotic women of vertebral fractures, which composition can be administered in a protocol over a three year period.

The composition can also be used in combination with prostaglandins (see WO 94/06750), estrogen (see WO 94/14455), or growth hormone secretagogues to treat osteoporosis and the above-described conditions associated with abnormalities in bone resorption.

The following Example is given to illustrate the carrying out of the invention as contemplated by the inventors and should not be construed as being a limitation on the scope and spirit of the invention.

EXAMPLE

Preparation of 4-Amino-1-Hydroxy-Butylidene-1,1-Bisphosphonic Acid Monosodium Salt Anhydrate To a suspension of 4-amino-1-hydroxy-1,1-diphosphonic acid (4.02 g) in 150 ml of distilled water was added with stirring aqueous sodium hydroxide (0.5N) until the pH of the solution was 4.40. The stirred solution was triturated with 200 ml ethanol (absolute) to give a suspension of a fine white solid which was chilled at 5 degrees C. overnight. The obtained solid was collected by vacuum filtration, air dried, and then dried in vacuo at 100 degrees C. at 0.2 torr for 18 hours over $P_2O_5$ to yield 3.38 g, (91%) yield of the titled compound. A sample was submitted for CHN analysis;

For $C_4H_{12}NO_7P_2Na$:

Anal.: C, 17.72; H, 4.46; N, 5.16

Found: C, 17.56; H, 4.67; N, 5.15

Melting Point of the solid was 244–245 degrees C.(d.)

The obtained titled salt displays a unique X-ray diffraction pattern.

Solubility of the anhydrous monosodium salt in water is about 300 mg/ml as compared to the free acid which is 8 mg/ml. However, above 40 mg/ml, the trihydrate precipitates out of the aqueous solution.

The solution pH of the monosodium salt at 40 mg/ml. is 4.4, as compared to the free acid which is pH 2.2 at 8 mg/ml.

The water adsorption by the anhydrous salt at lower humidities is quite slow.

What is claimed is:

1. A method for treating bone resorption in a mammal in need thereof comprising administering to said mammal a therapeutically effective amount of anhydrous 4-amino-hydroxybutylidene-1,1-bisphosphonic acid monosodium salt in a pharmaceutically acceptable carrier.

2. A method for preventing bone resorption in a mammal in need thereof comprising administering to said mammal a therapeutically effective amount of anhydrous 4-amino-hydroxybutylidene-1,1-bisphosphonic acid monosodium salt in a pharmaceutically acceptable carrier.

3. A method for inhibiting bone resorption in a mammal in need thereof comprising administering to said mammal a therapeutically effective amount of anhydrous 4-amino-hydroxybutylidene-1,1-bisphosphonic acid monosodium salt in a pharmaceutically acceptable carrier.

4. A method for promoting bone growth in a mammal in need thereof comprising administering to said mammal a therapeutically effective amount of anhydrous 4-amino-hydroxybutylidene-1,1-bisphosphonic acid monosodium salt in a pharmaceutically acceptable carrier.

* * * * *

UNITED STATES PATENT AND TRADEMARK OFFICE
CERTIFICATE OF CORRECTION

PATENT NO: 6,008,207

DATED: 12/28/1999

INVENTOR(S): G.S. BRENNER et al.

It is certified that error appears in the above-identified patent and that said Letters Patent is hereby corrected as shown below:

IN THE CLAIMS:

At Col. 4, Claim 1, line 41, delete the compound "4-amino-hydroxybutylidene-1,1-bisphosphonic acid monosodium salt" and insert therefor -- 4-amino-1-hydroxybutylidene-1,1-bisphosphonic acid monosodium salt --.

At Col. 4, Claim 2, line 46, delete the compound "4-amino-hydroxybutylidene-1,1-bisphosphonic acid monosodium salt" and insert therefor -- 4-amino-1-hydroxybutylidene-1,1-bisphosphonic acid monosodium salt --.

At Col. 4, Claim 3, line 51, delete the compound "4-amino-hydroxybutylidene-1,1-bisphosphonic acid monosodium salt" and insert therefor -- 4-amino-1-hydroxybutylidene-1,1-bisphosphonic acid monosodium salt --.

At Col. 4, Claim 4, line 56, delete the compound "4-amino-hydroxybutylidene-1,1-bisphosphonic acid monosodium salt" and insert therefor -- 4-amino-1-hydroxybutylidene-1,1-bisphosphonic acid monosodium salt --.

Signed and Sealed this

Thirty-first Day of October, 2000

Attest:

Q. TODD DICKINSON

*Attesting Officer*  *Director of Patents and Trademarks*